United States Patent [19]

Isogai et al.

[11] Patent Number: 4,760,171

[45] Date of Patent: Jul. 26, 1988

[54] PROCESS FOR PRODUCING ETHANOL

[75] Inventors: Nobuo Isogai; Akitomo Uda; Kazuo Tanaka; Motoyuki Hosokawa, all of Niigata, Japan

[73] Assignee: Agency of Industrial Science and Technology, Tokyo, Japan

[21] Appl. No.: 32,257

[22] Filed: Mar. 31, 1987

[30] Foreign Application Priority Data

Dec. 10, 1986 [JP] Japan .................. 61-292425

[51] Int. Cl.$^4$ .................. C07C 29/00; C07C 31/08
[52] U.S. Cl. .................................... 568/902
[58] Field of Search .................... 568/902 H

[56] References Cited

U.S. PATENT DOCUMENTS

| | | | |
|---|---|---|---|
| 4,168,391 | 9/1979 | Slinkard et al. | 568/902 H |
| 4,190,729 | 2/1980 | Forster | 568/902 H |
| 4,262,154 | 4/1981 | Gane et al. | 568/902 H |
| 4,423,257 | 12/1983 | Isogsi et al. | 568/902 H |
| 4,424,383 | 1/1984 | Cornils et al. | 568/902 H |

FOREIGN PATENT DOCUMENTS

| | | | |
|---|---|---|---|
| 55-935 | 10/1981 | Japan . | |
| 1056140 | 3/1986 | Japan | 568/902 H |
| 39054 | 10/1978 | United Kingdom . | |
| 2036739 | 7/1980 | United Kingdom . | |

OTHER PUBLICATIONS

U.S. Ser. No. 289,405, Habib et al., 8-3-81.

Primary Examiner—J. E. Evans
Attorney, Agent, or Firm—Browdy and Neimark

[57] ABSTRACT

A process for producing ethanol which comprises reacting methanol, carbon monoxide and hydrogen in the presence of a catalyst comprising a cobalt phosphine carbonyl complex having the formula:

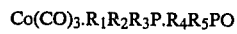

$Co(CO)_3 \cdot R_1R_2R_3P \cdot R_4R_5PO$ wherein each of $R_1$, $R_2$, $R_3$, $R_4$ and $R_5$ is independently hydrogen, $C_1$–$C_{20}$ alkyl, $C_3$–$C_{20}$ cycloalkyl or aryl, and the alkyl, cycloalkyl or aryl may contain a member selected from N, O, S, halogen and mixtures thereof is disclosed.

3 Claims, No Drawings

PROCESS FOR PRODUCING ETHANOL

This invention relates to a process for selectively producing ethanol from methanol, carbon monoxide and hydrogen. More particularly, this invention relates to a process for producing ethanol by using a catalyst comprising a cobalt phosphine carbonyl complex.

Processes for producing ethanol which comprise reacting methanol, carbon monoxide and hydrogen in the presence of a catalyst comprising cobalt and a phosphine are disclosed in UK Pat. No. 2,036,739, U.S. Pat. Nos. 4,424,383 and 4,168,391, UK Patent Appln. No. 39054/1978, U.S. Ser. No. 289,401/1981 and Japanese Patent Publication (kokai) No. 56-25121.

UK Pat. No. 2,036,739 discloses a process for producing ethanol which comprises reacting methanol, carbon monoxide and hydrogen in a hydrocarbon solvent in the presence of cobalt iodine catalyst or bromine-tertiary phosphine. UK Patent Appln. No. 39054/1978 and Japanese Patent Publication (kokai) No. 56-25121 disclose use of a multidentate ligand containing an element of Group Va, such as phosphorus, or arsenic in such catalyst. U.S. Pat. No. 4,424,383 and U.S. Ser. No. 289,405/1981 disclose use of a multi-dentate ligand containing an organic phosphine in a cobalt-ruthenium-iodine catalyst.

U.S. Pat. No. 4,168,391 discloses a process for producing ethanol from methanol, carbon monoxide and hydrogen by using a cobalt carbonyl catalyst excluding iodine and a non-polar compound solvent or inert oxygen-containing compound solvent.

Catalysts containing cobalt and a phosphine are prepared by one-step charging. When ethanol is produced by using such a catalyst, a considerable amount of such by-products as dimethyl ether, diethyl ether, acetaldehyde, dimethoxy ethane, acetic acid, ethyl acetate, ethyl formate and the like are produced. As a result, the selectivity to neat ethanol is low, and the reaction rate is unsatisfactory.

The catalyst prepared from cobalt and a phosphine by one-step charging contains a variety of complexes. Some of such complexes are not conducive to forming ethanol, that is they not only accelerate the formation of by-products, but also lower the activity of the catalyst and the selectivity to ethanol. These shortcomings cannot essentially be avoided by one-step charging process.

The present inventors conducted research on methods of producing ethanol by using a catalyst comprising cobalt and a phosphine. As a result, we have found that a cobalt phosphine carbonyl complex catalyst is effective in such a reaction. That is, the catalyst increases the substantial selectivity to ethanol and the reaction rate.

This invention relates to a process for producing ethanol which comprises reacting methanol carbon monoxide and hydrogen in the presence of a catalyst comprising a cobalt phosphine carbonyl complex having the formula:

$$Co(CO)_3 \cdot R_1R_2R_3P \cdot R_4R_5PO$$

wherein each of $R_1$, $R_2$, $R_3$, $R_4$ and $R_5$ is independently hydrogen, $C_1-C_{20}$ alkyl, $C_3-C_{20}$ cycloalkyl or aryl, and the alkyl, cycloalkyl or aryl may contain a member selected from N, O, S, halogen, and mixtures thereof.

The present catalyst may be prepared by bonding $R_1R_2R_3P$ ligand and $R_4R_5P(O)^-$ ligand to cobalt carbonyl. The present catalyst is novel and was discovered by the present inventors.

The structure of the catalyst is supported by $^1H$, $^{13}C$, $^{17}O$, $^{31}P$, NMR spectral, IR spectral, mass spectral, measuring of molecular weight, element analysis and the like. When $R_1-R_5$ have high molecular weight, it is difficult to form the complex.

PREPARATION OF THE CATALYST

First of all, a cobalt phosphine carbonyl complex is prepared. A cobalt compound and a phosphine compound are thermal-treated in a solvent under mixed gas (synthetic gas) of carbon monoxide and hydrogen at 0–500 kg/cm², preferably 50–300 kg/cm² and 100°–300° C., preferably 150°–250° C.

Examples of suitable cobalt compounds include cobalt carbonyl, such as dicobalt octacarbonyl, and cobalthydride tetracarbonyl; inorganic cobalt compounds, such as cobalt hydroxide, basic cobalt carbonate, and cobalt halide; organic cobalt compounds, such as cobalt organic acid salts, cobaltcene and cobalt acetyl acetonate; and other cobalt compounds capable of producing cobalt carbonyl in the reaction system.

Examples of suitable phosphines include alkyl, cycloalkyl or aryl phosphines, such as triethyl phosphine, tri-n-propyl phosphine, tri-n-butyl phosphine, tri-t-butyl phosphine, triphenyl phosphine, tricyclohexyl phosphine, bis(1,4-diphenyl phosphino)butane and bis(1,6-diphenyl phosphino)hexane. Compounds containing N, O, S or halogen, such as trisdimethylamino phosphine, tri-p-methoxyphenyl phosphine, tetramethyl biphosphine disulfide and tri-p-chlorophenyl phosphine can be used as the phosphine compounds.

The ratio of the cobalt carbonyl and the phosphine is important in the preparation of the cobaltcarbonyl phosphine complex. The ratio of cobaltcarbonyl to phosphine may be in the range of 1:1–10:1, preferably 1:1 to 5:1, in terms of the atomic ratio of cobalt to phosphorus. When the ratio is less than 1:1, the yield of the complex becomes lower. When the ratio is more than 10:1, the formation speed is low.

Preparation of the complex may be carried out in an inert solvent. Suitable inert solvents include hydrocarbons, ethers and esters. Examples of such hydrocarbons are aromatic hydrocarbons, such as benzene, toluene and xylene; aliphatic hydrocarbons, such as hexane and octane; and alicyclic hydrocarbons, such as cyclohexane. Ethers include, for example, dimethyl ether, diisopropyl ether, dioxane and tetrahydrofuran. Esters include, for example, methyl acetate, and ethyl acetate. The amount of solvent employed may be in the range of 0.1–300 mol, preferably 1–50 mol, per 1 gram-atom of cobalt.

The pressure used in the preparation may be in the range of 0–500 kg/cm². A pressure of 0 kg/cm² means the absence of carbon monoxide and hydrogen. That is, the cobalt complex can be formed in the absence of carbon monoxide and hydrogen. However, the yield of cobalt complex is low in the absence of CO and H₂. A pressure of more than 500 kg/cm² is not practical. Pressure of 50–300 kg/cm² is preferable.

The molar ratio of CO to H₂ may be in the range of 10:1 to 1:10, preferably 5:1 to 1:5. The carbon monoxide and hydrogen may contain argon, nitrogen, carbon dioxide, methane and ethane which are inert to the reaction. When the carbon monoxide and hydrogen contain these gas, the combined partial pressure of CO and H₂ is within the above-mentioned range.

The reaction temperature may be in the range of 100°–300° C., preferably 150°–250° C. The reaction temperature of less than 100° C. lowers the reaction speed. The temperature of more than 300° C. lowers yield of the complex.

The cobalt complex can be recovered from the reaction mixture by gel-chromatography.

It is preferable that the porous synthetic resins applicable in the chromatograph column have large surface area.

The size of the synthetic resin particles is not critical. It is also preferable that the resins have excellent mechanical strength and particularly anti-abrasion.

Examples of the industrially less expensive, non-polar or polar porous synthetic resins usable in the chromatograph column include non-polar resins, such as styrene-divinylbenzene copolymer (trade name, Amberlite XAD-2 and XAD-4, Rohm and Haas Co., trade name, Highporous Polymer HP, Nippon Rensui Co.); and polar resins, such as polyacryl resin (trade name, Amberlite XAD-7 and XAD-8, Rohm and Haas Co.), polysulfoxide (trade name, Amberlite XAD-9, Rohm and Haas Co.), and polyamide (trade name, Amberlite XAD-11, Rohm and Haas Co.)

Eluting agents usable in the chromatograph column include, for example, methanol, ethanol, isopropanol, n-propanol, acetone, methyl ethyl ketone, isopropyl ether, tetrahydrofuran, dioxane, ethyl acetate, benzene, toluene, hexane, petroleum ether, petroleum benzine, isopentane, carbon tetrachloride, chloroform, dimethyl formamide, methyl-t-butyl ether and water. Mixtures of these non-polar and polar solvents can be used.

When a non-polar porous synthetic resin, such as styrene-divinyl benzene copolymer is used, the catalytic components are adsorbed from a polar solvent, such as methanol followed by eluting the remaining components by a mixed solvent obtained by adding acetone to methanol to weaken polarity of methanol. When a polar porous synthetic resin, such as an acrylic acid ester polymer is used a non-polar solvent, such as hexane is used as an eluting agent.

After the eluting operation is completed, the column is regenerated by washing the column with a solvent which dissolves the catalytic components. Relatively non-polar organic solvents, such as acetone, isopropyl ether, benzene and the like are preferable.

PREFERABLE EMBODIMENT OF CHROMATOGRAPH COLUMN

A non-polar synthetic resin is used as a porous resin. A polar solvent, such as water, an alcohol, a ketone, dimethyl sulfoxide, dimethylformamide, acetonitrile and the like is used as an eluting agent. Mixed solvents of a $C_1$–$C_5$ alcohol and a $C_3$–$C_6$ ketone or mixed solvents of one of the alcohol and the ketone and an other solvent, such as mixtures of methanol-water, methanol-acetone, methanol-n-hexane or acetone-water are preferable.

The cobalt phosphine carbonyl complex [Co(CO)$_3$.R$_1$R$_2$R$_3$PO] of this invention can be used as a catalyst for producing ethanol without a co-catalyst. However, the complex may contain one or more of compounds of halogens, ruthenium, iron, nickel, manganese, rhenium, platinum, palladium and the like. The amounts of the halogen or the metal compounds which can be contained in the complex may be in the range of 0.001–2 gram-atom per 1 gram-atom of cobalt in terms of a halogen atom or a metal atom. The complex may also contain an organic acid, such as an aromatic carboxylic acid or an inorganic acid, such as sulfuric acid, sulfonic acid, selenic acid and the like.

CONDITIONS FOR REACTING METHANOL, CARBON MONOXIDE AND HYDROGEN

The molar ratio of carbon monoxide to hydrogen may be in the range of 5:1 to 1:5, preferably 3:1 to 1:3. The reaction pressure may be more than 50 kg/cm$^2$, preferably in the range of 100–500 kg/cm$^2$. The reaction temperature may be in the range of 180° C. to 280° C., preferably 200° C. to 250° C. Though the reaction proceeds at a temperature below 180° C., the reaction speed is low; at temperature above 280° C. by-products form.

The amount of catalyst employed may be in the range of 1–300 mg, preferably 5–100 mg per 1 mol of methanol in terms of cobalt atom. Though the reaction proceeds at the amount of catalyst of less than 1 mg, the reaction speed is low. At the amount of catalyst above 300 mg, it adds unnecessarily to the cost.

The present process can be carried out in the absence of any solvent.

Use of solvent is not critical in this invention. However, it is preferable that the reaction is carried out in the presence of solvents which do not have a bad influence on the reaction.

Solvents which are inert to the reaction system include hydrocarbons and ethers. Hydrocarbon solvents include, for example, aromatic hydrocarbons, such as toluene, benzene and xylene; aliphatic hydrocarbons, such as hexane and octane; and alicyclic hydrocarbons, such as cyclohexane. The ethers include, for example, diethyl ether, dioxane, tetrahydrofuran and the like.

The amount of the solvent employed may be in the range of 0–5 mol, preferably 0–2 mol per 1 mol of methanol. Use of solvent in an amount of more than the above upper limit lowers the space time yield of ethanol and is not practical.

The present invention can be carried out either as a batch process or as a continuous process.

EFFECTIVENESS OF INVENTION

The present inventors have found that cobalt phosphine carbonyl catalyst [Co(CO)$_3$.R$_1$R$_2$R$_3$P.R$_4$R$_5$PO] is effective for producing ethanol from methanol, carbon monoxide and hydrogen. The cobalt phosphine carbonyl separated from the reaction mixture exhibits high catalytic activity and high selectivity to ethanol. The present catalysts have excellent industrial significance. The complex is a novel compound which the present inventors have found.

The cobalt-phosphine complex prepared by one-step charging in the prior art contains a variety of complexes, so some of such complexes are not conductive to forming ethanol, that is they lower activity of the catalyst and the selectivity to ethanol. These shortcomings cannot essentially be avoided in the catalyst prepared by one-step charging.

According to the present invention, only effective cobalt-carbonyl complex is separated by a gel-chromatography, so above-mentioned shortcomings can be avoided by the present invention. The complex of this invention separated by a gel-chromatography exhibits high catalytic activity and selectivity to ethanol. In addition, an effective complex catalyst can be recovered from the waste catalytic solution by a gel-chromatography. The present process does not need corrosive halogen compounds or other metal compounds. In addition, a high space time yield of ethanol and high selectivity to ethanol can be attained according to the present invention.

The present invention is further illustrated by nonlimiting Examples and Comparative Runs.

In the following Examples and Comparative Runs, the reactivity of methanol, selectivity to ethanol, and selectivity to realizable ethanol are expressed by the following equations.

Reactivity of methanol (%) =

$$\frac{\text{mol of CH}_3\text{OH fed} - \text{mol of unreacted CH}_3\text{OH}}{\text{mol of CH}_3\text{OH fed}} \times 100$$

Selectivity to ethanol (%) =

$$\frac{\text{mol of CH}_3\text{OH converted to ethanol}}{\text{mol of CH}_3\text{OH fed} - \text{mol of unreacted CH}_3\text{OH}} \times 100$$

Selectivity to realizable ethanol (%) =

$$\frac{\text{mol of neat ethanol} + \text{mol of ethanol converted}^{*1}}{\text{mol of CH}_3\text{OH fed} - \text{mol of unreacted CH}_3\text{OH} -} \times 100$$

mol of CH$_3$OH converted$^{*2}$

*[1] means components, such as acetaldehyde, dimethoxy ethane, ethyl esters, etc., from which ethanol can easily be recovered through hydrogenation or hydrolysis
*[2] means components, such as dimethoxy ethane, methyl esters, etc. from which methanol can easily be recovered through hydrolysis

EXAMPLE 1

(1) PREPARATION OF CATALYTIC SOLUTION AND ACTIVATION TREATMENT THEREOF

Into a 500 ml stainless steel stirrer autoclave were charged 100 g of benzene, 15.2 g of basic cobalt carbonate (2CoCO$_3$.3Co(OH)$_2$.H$_2$O) (0.117 gram-atom of Co) and 47.3 g (0.234 mol) of tri-n-butylphosphine. The autoclave was closed. Mixed gas of H$_2$ and CO (molar ratio of 1:1) was fed to pressure of 200 kg/cm$^2$. The activation was effected at 230° C. for 1.5 hours, and the mixture was cooled. The gas remaining in the autoclave was discharged.

(2) SEPARATION OF EFFECTIVE COMPLEX

The mixture was withdrawn from the autoclave and was charged into a rotary evaporator. Benzene (solvent) was removed from the mixture under a nitrogen atmosphere at 60° C. and 60 mmHg to obtain viscous solution 70 g of the solution was dissolved in 0.5 liter of methanol. Into a 65$^\phi$×900$^L$ glass column was charged 1.5 liter of non-polar, porous resin, Highporous Polymer HP-20 (trade name, Nippon Rensui Co.) in methanol. A sufficient amount of methanol was passed through the column. Thereafter, a solution of the complex of step (1) in methanol was passed through the column. Yellow to orange gel was observed on the resin. This shows that effective components was selectively absorbed into or onto the resin. Mixed solvent of methanol and acetone (volume ratio of 1:1) was passed through the column to elute the effective components. The resulting solution (2 l) was concentrated and dried to obtain an effective catalyst solid. $^1$H, $^{13}$C, $^{17}$O, $^{31}$P NMR spectral, IR spectral, mass spectral, element analysis, etc. showed that the complex has chemical structure of Co(CO)$_3$.(n-C$_4$H$_9$)$_3$P.(n-C$_4$H$_9$)$_2$PO.

(3) TEST FOR EVALUATING ACTIVITY OF CATALYST

Into a 100 ml stainless steel shaking autoclave were charged 5.9 g (0.0117 mol) of the complex catalyst of step (2), 10 g (0.3121 mol) of methanol and 10 g of benzene. A mixed gas of H$_2$ and CO (molar ratio of 1:1) was fed into the autoclave until a pressure of 200 kg/cm$^2$G was reached. The mixture was maintained at 230° C. for 15 minutes. Thereafter the autoclave was cooled and the gas remaining in the autoclave was discharged to the atmosphere. Gas Chromatograph (GC) Analysis (internal standard method) showed the reactivity of methanol to be 43.2% and a selectivity to neat ethanol of 91.3%. The analysis also showed that by-products, such as acetaldehyde, dimethoxy ethane, methyl ethyl ether, methyl acetate, propanol, etc. are present in the reaction product.

This shows selectivity to realizable ethanol of 93.8%.

EXAMPLE 2

The procedure of steps (1) and (2) of Example 1 was repeated except that tri-n-propyl phosphine was used instead of tri-n-butyl phosphine. The resulting complex had a chemical structure of Co(CO)$_3$.(n-C$_3$H$_7$)$_3$P.(n-C$_3$H$_7$)$_2$PO.

(3) Into a 100 ml stainless steel shaking autoclave were charged 5.2 g (0.0117 mol) of the complex catalyst of the above steps, 10 g (0.3121 mol) of methanol and 10 g of benzene. A mixed gas of H$_2$ and CO (molar ratio of 1:1) was fed into the autoclave until a pressure of 200 kg/cm$^2$G was reached. The mixture was maintained at 230° C. for 15 minutes. Thereafter the autoclave was cooled and the gas remaining in the autoclave was discharged to the atmosphere. Gas Chromatograph (GC) Analysis (internal standard method) showed the reactivity of methanol to be 34.0% and a selectivity to neat ethanol of 85.2%. The analysis also showed that by-products, such as acetaldehyde, dimethoxy ethane, methyl ethyl ether, methyl acetate, propanol, etc. are present in the reaction product.

This shows selectivity to realizable ethanol of 90.4%.

COMPARATIVE RUN 1

The catalytic solution of step (1) of Example 1 was used in step (3) without carrying out chromatographic separation. The procedure of step (3) of Example 1 was repeated except that the reaction time was 1.5 hours. The results are shown in the following:

| | |
|---|---|
| Reactivity of methanol: | 25.3% |
| Selectivity to neat ethanol: | 80.2% |
| Selectivity to realizable ethanol: | 85.0% |

The reaction speed in Example 1 was 10 times of that in Comparative Run 1. The selectivity to realizable ethanol of Example 1 was by about 8% higher than that of Comparative Run 1.

COMPARATIVE RUN 2

The catalytic solution of step (1) of Example 2 was used in step (3) without carrying out chromatographic separation. The procedure of step (3) of Example 2 was repeated except that the reaction time was 1.5 hours. The results are shown in the following:

| | |
|---|---|
| Reactivity of methanol: | 26.4% |
| Selectivity to neat ethanol: | 73.1% |
| Selectivity to realizable ethanol: | 76.0% |

The reaction speed in Example 2 was 8 times of that in Comparative Run 2. The selectivity to realizable ethanol of Example 2 was about 14% higher than that of Comparative Run 2.

What is claimed is:

1. A process for producing ethanol which comprises reacting methanol, carbon monoxide and hydrogen in the presence of a catalyst effective component separated through chromatography from the reaction mixture of a cobalt compound and a phosphine, the catalyst comprising a cobalt phosphine carbonyl complex having the formula:

$$Co(CO)_3.R_1R_2R_3P.R_4R_5PO$$

wherein each of $R_1$, $R_2$, $R_3$, $R_4$ and $R_5$ is independently hydrogen, $C_1$–$C_{20}$ alkyl, $C_3$–$C_{20}$ cycloalkyl or aryl, and the alkyl, cycloalkyl or aryl may contain a member selected from N, O, S, halogen and mixtures thereof.

2. The process of claim 1 wherein the catalyst is $Co(CO)_3.(n\text{-}C_4H_9)_3P.(n\text{-}C_4H_9)_2PO$.

3. The process of claim 1 wherein the catalyst is $Co(CO)_3.(n\text{-}C_3H_7)_3P.(n\text{-}C_3H_7)_2PO$.

* * * * *